United States Patent [19]

Hammersley

[11] Patent Number: 5,282,463
[45] Date of Patent: Feb. 1, 1994

[54] ANTI-DISCONNECT APPARATUS AND METHOD, FOR BREATHING SYSTEMS

[75] Inventor: Gerald L. Hammersley, West Hills, Calif.

[73] Assignee: Hammer-Plane, Inc., Simi Valley, Calif.

[21] Appl. No.: 759,881

[22] Filed: Sep. 13, 1991

[51] Int. Cl.⁵ ............................................. A61M 16/00
[52] U.S. Cl. ........................ 128/207.15; 128/207.17; 128/912; 128/DIG. 26
[58] Field of Search .................. 128/200.26, 207.14, 128/207.15, 207.17, 202.27, 912, DIG. 26

[56] References Cited

U.S. PATENT DOCUMENTS

| | | | |
|---|---|---|---|
| 1,835,757 | 12/1931 | Burchett | 128/207.17 |
| 2,765,792 | 10/1956 | Nichols | 128/207.17 |
| 3,039,469 | 6/1962 | Fountain | 128/207.17 |
| 3,236,236 | 1/1966 | Hudson | 128/207.17 |
| 3,688,774 | 9/1972 | Akiyama | 128/200.26 |
| 3,946,742 | 3/1976 | Eross | 128/207.17 |
| 3,973,569 | 8/1976 | Sheridan et al. | 128./DIG. 26 |
| 3,987,798 | 10/1976 | McGinnis | 128/207.17 |
| 4,235,229 | 11/1980 | Ranford et al. | 128/912 |
| 4,256,099 | 3/1981 | Dryden | 128/200.26 |
| 4,304,228 | 12/1981 | Depel | 128/912 |
| 4,313,437 | 2/1982 | Martin | 128/207.17 |
| 4,331,144 | 5/1982 | Wapner | 128/207.17 |
| 4,485,822 | 12/1984 | O'Connor et al. | 128/DIG. 26 |
| 4,598,705 | 7/1986 | Lichtenberger | 128/200.26 |
| 4,641,646 | 2/1987 | Schultz et al. | 128/DIG. 26 |
| 4,848,331 | 7/1989 | Northway-Meyer | 128/200.26 |
| 4,906,234 | 3/1990 | Voychehovski | 604/79 |
| 5,009,227 | 4/1991 | Nieuwstad | 128/200.26 |
| 5,042,477 | 8/1991 | Lewis | 128/DIG. 26 |
| 5,054,482 | 10/1991 | Bales | 128/207.17 |
| 5,056,515 | 10/1991 | Abel | 128/207.15 |
| 5,069,206 | 12/1991 | Crosbie | 128/DIG. 26 |
| 5,123,410 | 6/1992 | Greene et al. | 128/DIG. 26 |

*Primary Examiner*—Edgar S. Burr
*Assistant Examiner*—Aaron J. Lewis
*Attorney, Agent, or Firm*—William W. Haefliger

[57] ABSTRACT

In a tracheostomy tube structure, a neckplate of the tube structure and on elbow dis-connectible from the structure, the steps include providing flexible band means, attaching the band means to the neckplate, extending the band means to retain the elbow, and tightening the band means to hold the elbow against inadvertent disconnection from the tube structure.

19 Claims, 3 Drawing Sheets

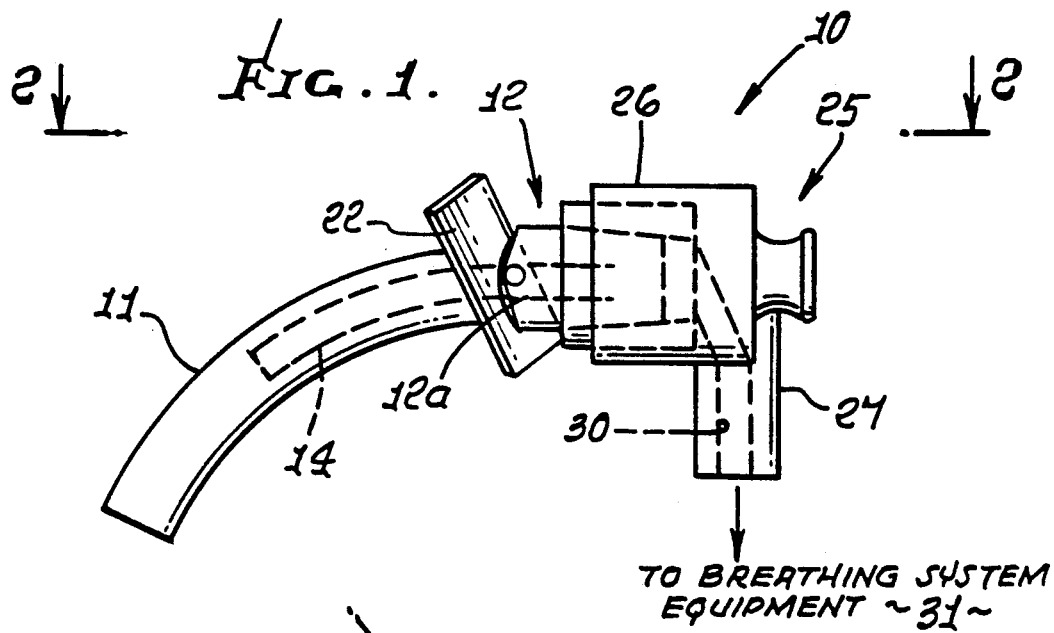
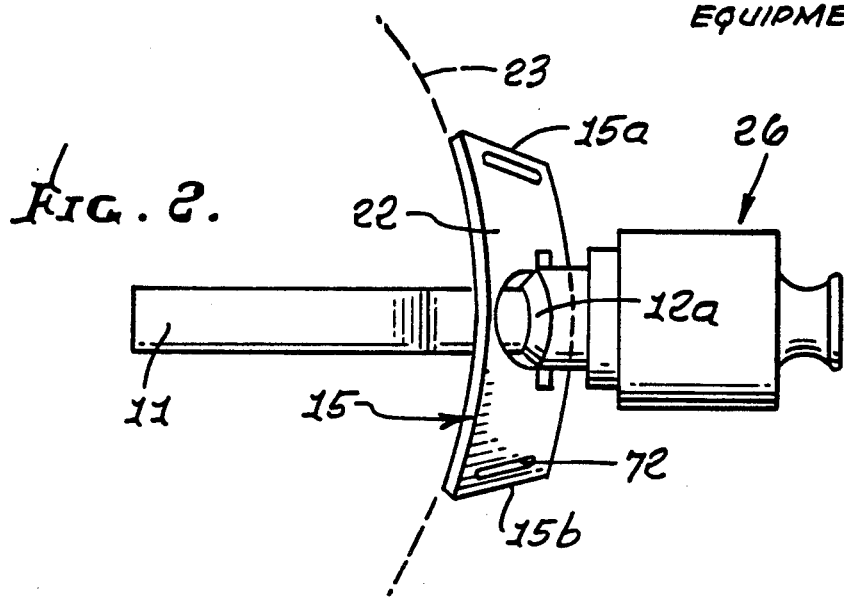
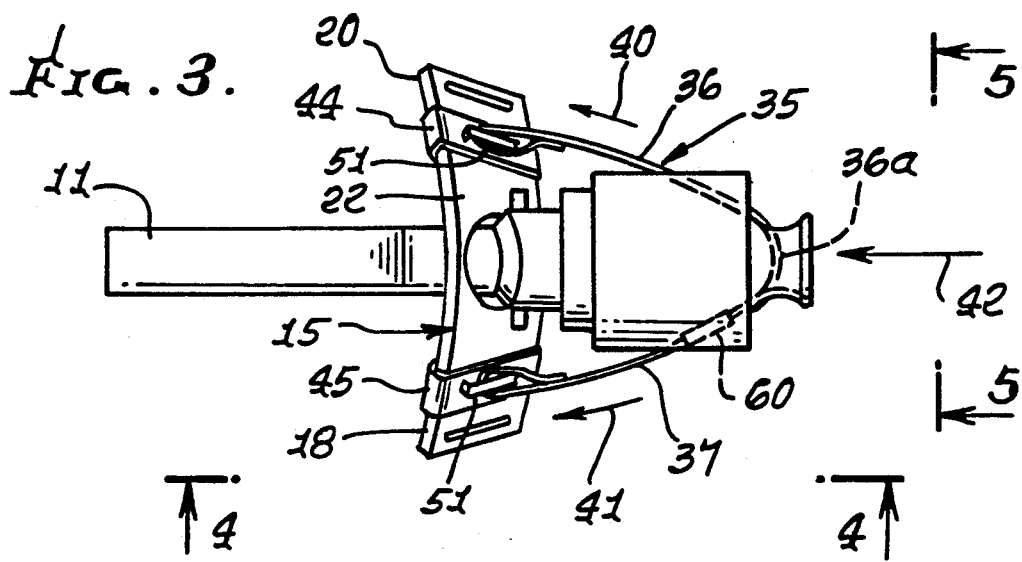

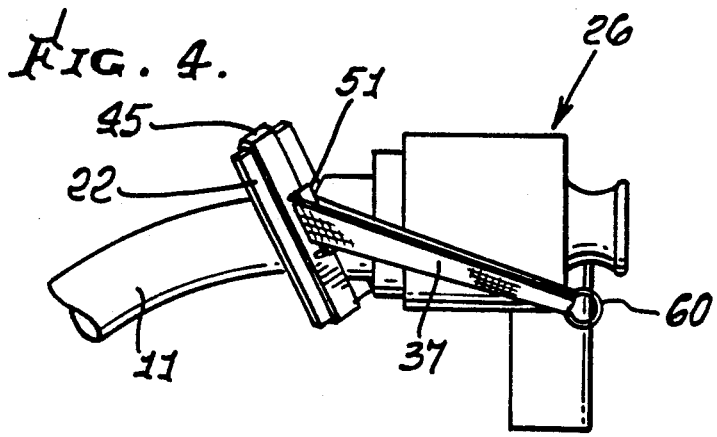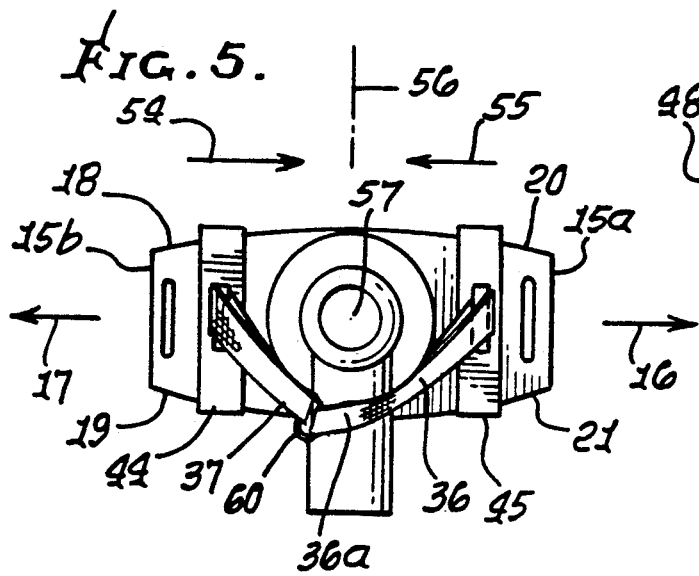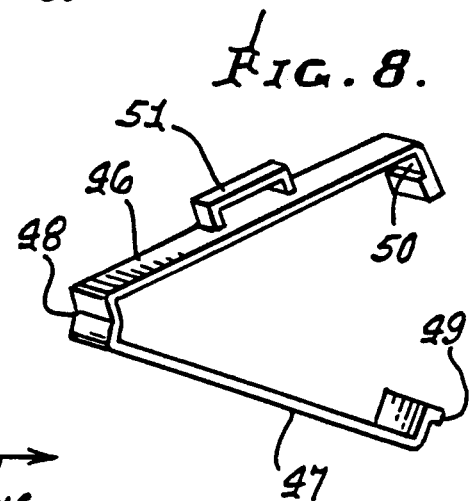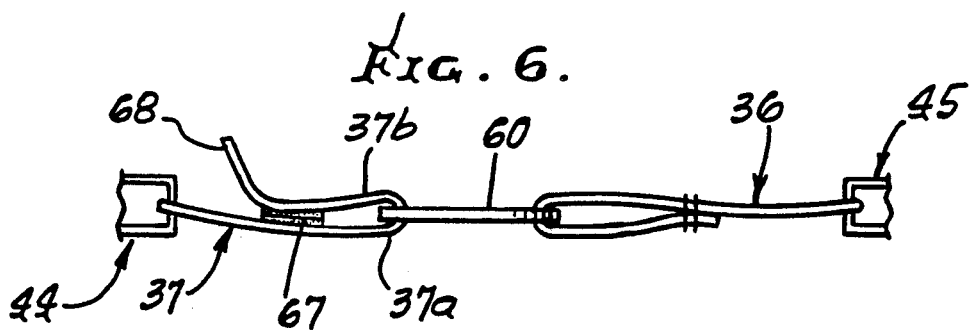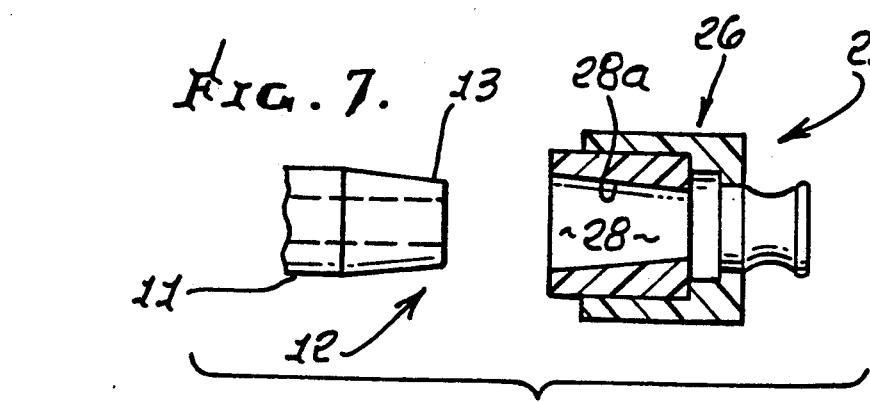

TO VENTILATOR

ANTI-DISCONNECT APPARATUS AND METHOD, FOR BREATHING SYSTEMS

BACKGROUND OF THE INVENTION

This invention relates generally to use of tracheostomy tubes and associated equipment; and more particularly is addressed to the problem of inadvertent disconnection of elements of such equipment which can lead to unwanted interruption of breathing. This problem becomes acute when the patient cannot reconnect the disconnected elements.

According to a report produced by Arthur D. Little Inc. for the FDA in 1986, there is an on going problem of accidental breathing systems disconnections. Among the conclusions in this report was the determination that no adequate anti-disconnection devices were currently available.

Recently, in 1991 *Progress Notes*, a noted respiratory publication stated that the problem of accidental disconnections still exists. Suggestions were made, including the use of A.D.s (anti-disconnects).

Available A.D. systems have some fundamental flaws or draw backs that would be likely to prevent their acceptance by users. In particular, the flaws in most systems include:
1. they are cumbersome,
2. they are difficult to manipulate,
3. they require two-handed operation.

The current "state of the art" in anti-disconnect devices involves the use of rubberbands, which present the following problems:
1. They are difficult to apply to tracheostomy tubes.
2. In "single-limb" circuits the use of rubberbands increases the possibility of morbidity and mortality. This is caused by the possibility of disconnect and inadvertent cancellation of the lowpressure alarm. This is directly related to the use and failure of the rubberbands.

Their removal requires two handed manipulation.

SUMMARY OF THE INVENTION

It is a major object of the invention to provide method and means for preventing inadvertent disconnection of breathing system tubing from associated tracheostomy tubes. Basically, use is made of a neckplate usually carried by the tracheostomy tube, and an elbow frictionally and telescopically connectible to the tube, as will be seen. In this environment, the basic combination of the invention includes:

a) a flexible band means attachable to the neckplate, b) the band means having sufficient length to fit over the elbow, c) and tightening means engaging the band means, enabling manual tightening of the band means between the duct and the neckplate, thereby to hold the duct against inadvertent disconnection from the tube structure or neckplate.

As will be seen, the band means typically includes band sections, the tightening means for example including loop means to which one band section is connected, another band section extending through the loop means and back upon itself for releasable attachment. VELCRO elements may be provided on the other band section for releasable engagement to hold the other band section in tensioned condition after tightening.

Clip means may be attached to the band means, the clip means sized to fit onto the neckplate; and the clip means may include two clips, the band means having two sections respectively attached to the two clips, the clips attachable to two neckplate wings, respectively so that the two band sections exert balanced retention forces at opposite sides of said duct.

Yet another object includes the provision of tightening means which includes loop means to which said two band sections are connected, one band section slidably connected to the loop means.

As will also be seen, each clip may include two legs interconnected by a hinge, and having a detent connection to hold the clip closed on the wing to which it is attached. A channel may be provided on one leg to retain a band section.

These and other objects and advantages of the invention, as well as the details of an illustrative embodiment, will be more fully understood from the following specification and drawings, in which:

DRAWING DESCRIPTION

FIG. 1 is a side elevational view of a tracheostomy tube, neckplate and elbow;

FIG. 2 is top plan view taken on lines 2—2 of FIG. 1;

FIG. 3 is a view like FIG. 2, but also showing retention means attached to the elbow and neckplate;

FIG. 4 is a side elevational view taken on lines 4—4 of FIG. 3;

FIG. 5 is an end elevational view taken on lines 5—5 of FIG. 4;

FIG. 6 is a schematic view showing elements of the retention system;

FIG. 7 is an exploded view showing tracheostomy tube and elbow elements, and interengageable surfaces thereof;

FIG. 8 is a view of a clip;

DETAILED DESCRIPTION

Figure 9:
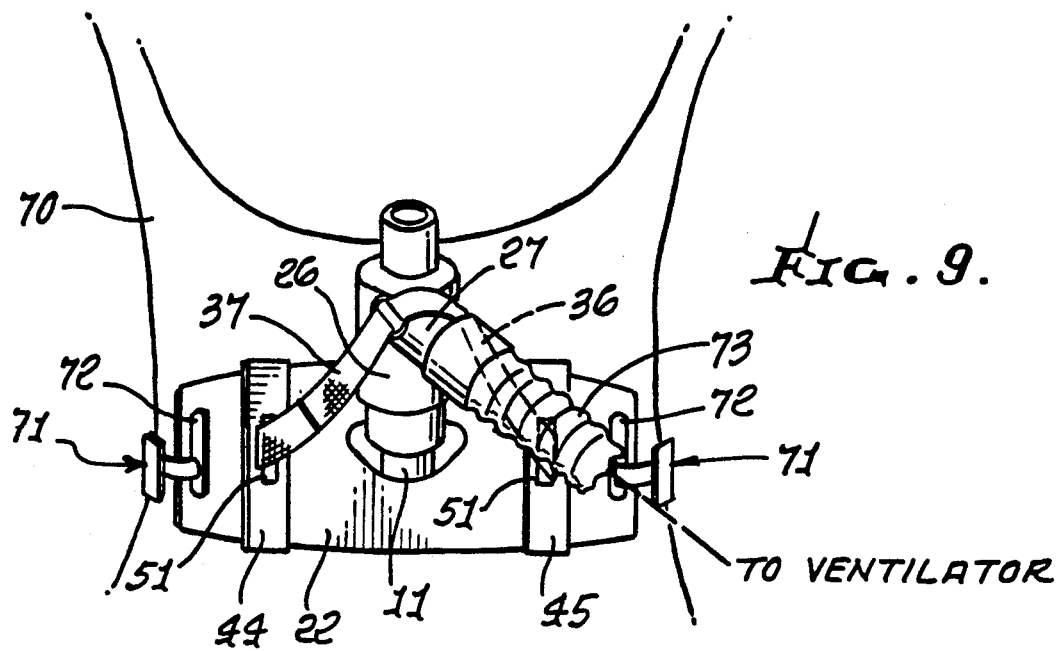
FIG. 9 is another view of equipment incorporating the invention.

In FIGS. 1, 2 and 7, a tracheostomy tube assembly 10 includes an elongated curved outer tube section 11 terminating at an enlarged tubular head section 12 having a tapering exterior surface 13 which is frusto-conical and tapers rightwardly. The assembly 10 also commonly includes an inner tube 14 communicating with end 12. A neckplate 15 is carried by the leftward extent 12a of section 12, to extend at opposite sides thereof, as further seen in FIGS. 2 and 3. The plate has wings 15a and 15b which project oppositely, and which narrow in width, in opposite directions 16 and 17. Wing edges appear at 18–21. Edges 18 and 19 taper in direction 17, and edges 20 and 21 taper in direction 16. The plate also has face 22 curvature to fit on a patient's neck 23, when tube section 11 is received through a neck opening and into the trachea. Various other forms of neckplates may be used.

A duct such as an elbow or bend 25 has legs 26 and 27, leg 26 defining a tubular socket 28 for reception of the surface 13 of head 12, the socket being rightwardly tapered at interior surface 28a of the socket, for telescopic press-together friction fitting and retention of the surfaces 13 and 28a; however, such surfaces can become inadvertently disconnected or disengaged. Note also that the elbow leg 27 extends downwardly, and has a bore 30 communicating with the tubular socket to pass air from breathing system 31 to the tube 11.

In accordance with the invention, the following are provided:

a) a flexible band means attachable to said neckplate, b) the band means having sufficient length to retain said elbow, c) and tightening means engaging the band means, enabling manual tightening of the band means between the elbow and said neckplate, thereby to hold the elbow against inadvertent disconnection from the tube structure.

In the illustrated example, the band means 35 includes band sections, such as section 36 and section 37 respectively extending at generally opposite sides of the elbow in FIG. 5. The two sections may consist of non-stretch fabric, for example. Section 36 also wraps part way about the elbow, at 36a. The two sections are connected to the neckplate wings 15a and 15b so as to provide elbow retention force along two directions 40 and 41 at opposite sides of the elbow, thereby to provide a force vector 42 extending along the central axis defined by the surfaces 13 and 28a, to prevent elbow leg 26 dis-connection from 12.

More specifically, two clips 44 and 45 are provided to attach the band sections 36 and 37 to the neckplate wings. Each clip is generally loop-shaped, as seen in FIG. 8, and has legs 46 and 47 to extend at opposite sides of the wing, and widthwise thereof. A hinge 48 is provided at one end of each leg, and may consist of a thinned section of plastic material, the legs consisting of relatively thicker plastic material. A snap detent connection is provided at the opposite ends of the legs, and includes tongue 49 on leg 47 and groove 50 on leg 46. A holder channel 51, molded on leg 46 is adapted to connect to one of the band sections 36 and 37, as better seen in FIG. 5, as for example by looping the band section through the channel. Since the wings are tapered, they limit sliding of the clips along the wings as in response to inward force exertion by the band sections in directions 54 and 55 in FIG. 5, whereby the clips are positioned at equal lateral distances from a plane 56 through axis 57 defined by 13 and 28a, for balanced retention force exertion.

Finally, the tightening means includes loop means, as for example a metallic ring 60, to which one band (band 36) is fixedly connected. The other band section 37 extends slidably through the loop, and is doubled back upon itself for releasable and adjustable attachment, to create retention force represented by vector 42 in FIG. 3. See FIG. 6, in these regards, and showing band section 37 having stretch 37a extending from clip 44 to the loop, and stretch 37b doubled back for attachment to stretch 37a at 67. Such attachment may be provided by interengageable VELCRO sections (hook and loop) on the respective band stretches. The stretch 37b has a free end 68 allowing quick pull-free of the stretches, for loop adjustment (tightening or loosening) as desired. A single band having two band sections can alternatively be adjustably attached to one or both clips, at the neckplate.

The basic method of use includes the steps:
a) providing flexible band means,
b) attaching the band means to the neckplate,
c) extending the band means over the elbow,
d) and tightening the band means to hold the elbow against inadvertent, disconnection from the neckplate tube structure.

Additional method steps include attaching two clips to neckplate wings, attaching two band sections to the clips to extend at opposite sides of the elbow, and create balanced retention force, for all tightening conditions.

Figure 10:
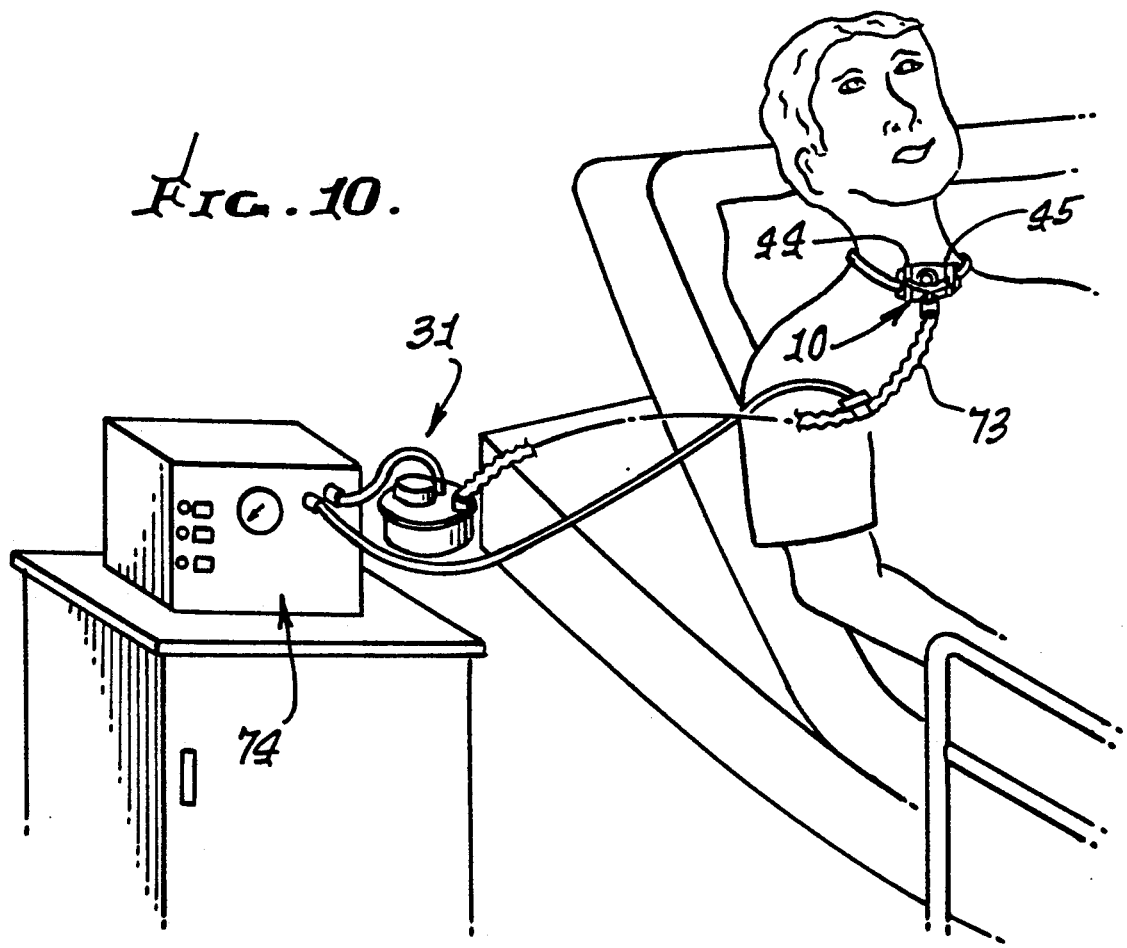
FIG. 10 is a view of a system incorporating the invention.

In FIG. 9, the assembly 10 is shown in perspective, as applied to a patient's neck 70. Neckplate 15 is held to the neck 70 by a retainer 71 attached to slots 72 in opposite ends of the neckplate. Corrugated tubing 73 fits on and extends from the elbow 27 to a ventilator apparatus 74 better seen in FIG. 10. Tubing 73 represents a single limb breathing circuit in the breathing apparatus indicated at 31, in FIG. 10.

I claim:

1. The method that includes the steps
    a) providing a tracheostomy tube structure, a neckplate on said tube structure and a duct disconnectible from the tube structure, the neckplate provided to have two wings,
    b providing flexible bands means, and providing two clips attached to said band means,
    c attaching said band means to said neckplate by releasably attaching said clips to said wings, respectively,
    d extending said band means to retain said duct,
    e and tightening said band means to hold said duct against inadvertent disconnection from said tracheostomy tube,
    f the clips provided to have operative connection to the duct only through the band means.

2. The method of claim 1 wherein said band means includes band sections, loop means being provided to which one of the band sections is connected, and said tightening step includes extending another band section through the loop means to be directed back upon itself for releasable attachment.

3. The method of claim 2 including providing VELCRO elements on said other band section for releasable engagement after the other band is pulled to tighten the band structure.

4. The method of claim 2 including releasably attaching said other band section to itself in spaced relation to the loop, and so as to provide said other band section with a free end portion to be manually graspable to be pulled for detaching the other band section from itself.

5. The method of claim 1 including preliminarily endwise interfitting the duct to said tracheostomy tube structure.

6. The method of claim 1 including providing clip means to interfit the neckplate, and attaching the band means to said clip means.

7. The method of claim 6 including adjustably positioning said two clips onto said two wings defined by the neckplate to create a force vector acting to hold the duct centrally onto the tracheostomy tube.

8. The method of claim 1 wherein the band means includes two sections, and including attaching one band section to one clip, and attaching the other band section to the other clip.

9. The combination of claim 1 wherein said duct comprises an elbow.

10. A tracheostomy tube structure comprising a tracheostomy tube, a neckplate carried on said tracheostomy tube, a duct having a tubular portion for endwise attachment to said tracheostomy tube, the combination comprising
    a) a flexible band means attachable to said neckplate,
    b) the band means having sufficient length to retain said duct, c) and tightening means engaging said band means, enabling manual tightening of the band means between the duct and said neckplate, thereby to hold the duct against inadvertent disconnection from said neckplate, d) the neckplate having two oppositely extending wings, there being two clips respectively attached to said wings, the band means having two sections respectively attached to the clips, each clip having two legs and retention means thereon releasably attached to a wing so that the two band sections exert retention force at opposite sides of the duct, e) the clips having opposite connection to the duct only through the band means.

11. The combination of claim 10 wherein said band means includes band section, the tightening means including loop means to which one band section is connected, another band section extending through the loop means and back upon itself for releasable attachment.

12. The combination of claim 11 including VELCRO elements on said other band section for releasable engagement to hold the other band section in tensioned condition after tightening.

13. The combination of claim 10 wherein said band means is wrapped about the duct and said band means is adjustably attached to said neckplate via said clip legs, for holding the duct in interfitted condition to the tube structure.

14. The combination of claim 13 wherein said duct and tube structure having interfitting frusto-conical tapered surfaces, the band means exerting force along two directions at opposite sides of said interengaged surfaces.

15. The combination of claim 10 wherein said tightening means includes loop means to which said two band sections are connected, one band section slidably connected to the loop means.

16. The combination of claim 10 wherein the two legs of each clip are interconnected by a hinge, and having a detent connection to hold the clip closed on the wing to which it is attached, there being a channel on one leg to retain a band section.

17. The combination of claim 10 wherein the neckplate wings are widthwise tapered to limit assembly of the clips onto the wings.

18. The combination of claim 10 wherein said duct comprises an elbow.

19. A tracheostomy tube structure comprising a tracheostomy tube, a neckplate carried on said tracheostomy tube, a duct having a tubular portion for endwise attachment to said tracheostomy tube, the combination comprising a) a flexible band means attached to said neckplate, the neckplate having two wings, there being at least one clip attached to said band means, said one clip having legs releasably attached to one of said neckplate wings whereby the band means is releasably attached to the neckplate, b) the band means having sufficient length to retain said duct, c) the band means adjusted to be tightened between the duct and said neckplate thereby to hold the duct against inadvertent disconnection from said neckplate, d) said duct and tube structure having interfitting surfaces, the band means exerting force along two directions at generally opposite sides of said interfitting surfaces, e) said band means extending toward said neckplate at said generally opposite sides of said interfitting surfaces, f) and there being connection lugs on the legs of said one clip, said legs being relatively movable, g) the clips having operative connection to the duct only through the band means.

* * * * *